Aug. 14, 1962 R. G. JELLY Plant Pat. 2,164
ROSE PLANT
Filed Sept. 29, 1961
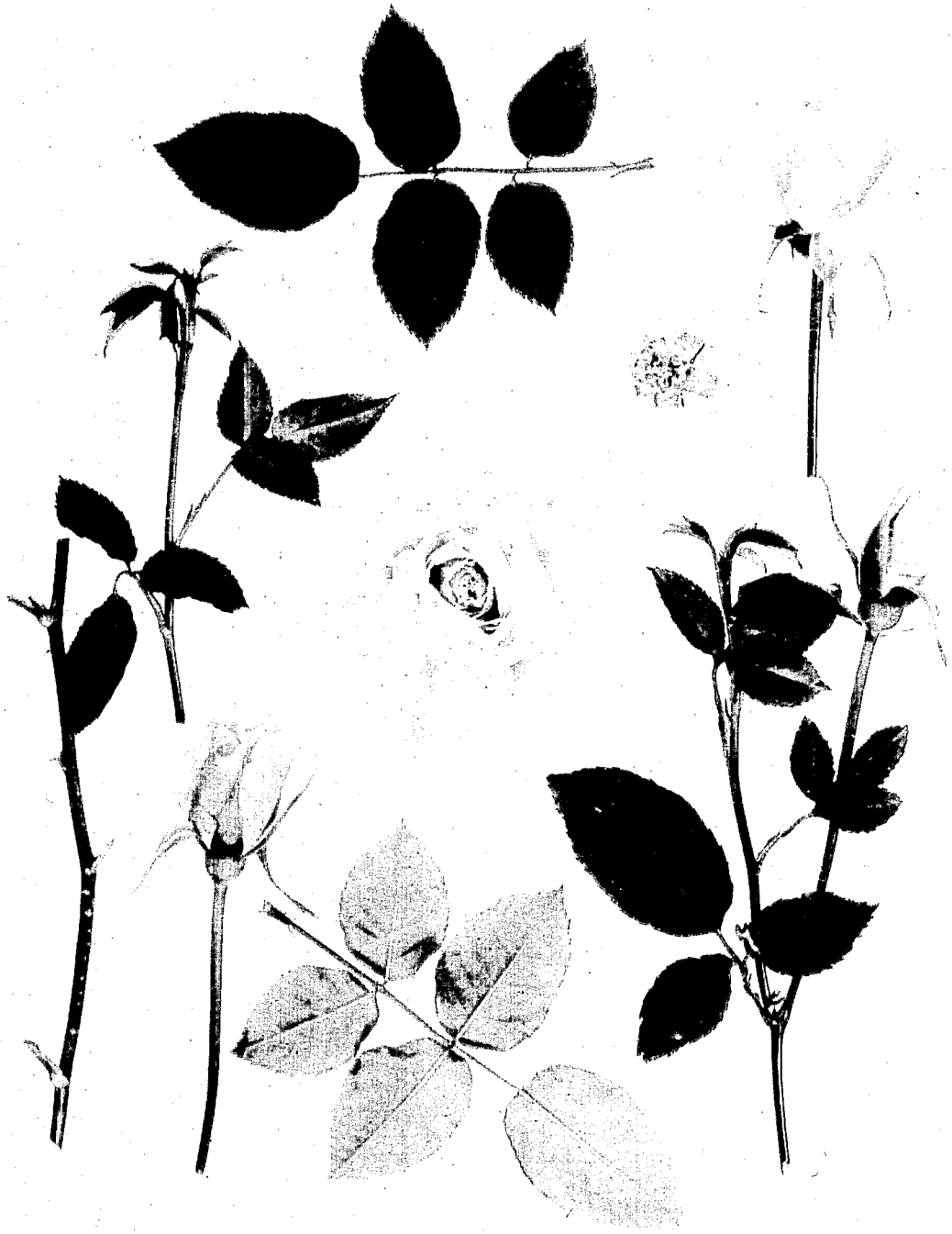
INVENTOR
Robert G. Jelly
BY Robb & Robb
ATTORNEYS United States Patent Office Plant Pat. 2,164
Patented Aug. 14, 1962

2,164
ROSE PLANT

Robert G. Jelly, Richmond, Ind., assignor to E. G. Hill Co., Inc., Richmond, Ind., a corporation of Indiana Filed Sept. 29, 1961, Ser. No. 141,923
1 Claim. (Cl. 47—61)

The present invention relates to a new and distinct variety of rose plant of the floribunda class, which was originated by me by crossing the variety "Garnette" (unpatented) with an unnamed and unpatented Pink Sweetheart seedling of "Garnette."

The primary objective of this breeding was to produce a new rose variety of the Pink Sweetheart type which would combine the excellent keeping qualities of the flowers of the parent variety "Garnette," with an improved flower stem length, as well as a pink flower color, rather than the red color of the flowers of the parent variety. This objective was fully achieved, along with other desirable improvements, as evidenced by the following unique combination of characteristics which are outstanding in the new variety and which distinguish it from its parents, as well as from all other varieties of which I am aware:

(1) Good length of flower stems suitable for cut flowers;

(2) Attractive and well-formed buds of large and commercially usable size;

(3) A distinctive and attractive pink general color tonality of the flowers; and (4) Good keeping qualities of the flowers.

In comparison with its seed parent "Garnette," the new variety has a greater flower stem length, larger buds of very excellent form, and the flower color is quite different, being pink instead of red.

As compared with the unnamed seedling pollen parent, the new variety has better plant growth, better stem length, and better color.

Asexual reproduction of the new variety by grafting, as performed at Richmond, Indiana, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Robert Ridgway's Color Standards and Nomenclature (hereinafter abbreviated as "R"), Robert S. Wilson's Horticultural Colour Chart (hereinafter abbreviated as "W"), and Nickerson Color Fan (hereinafter abbreviated as "N"), as indicated, except where general color terms of ordinary dictionary significance are obvious:

Type: Seedling; greenhouse; for cut flowers.
Class: Floribunda.
Breeding: Seedling.
*Seed parent.*—"Garnette."
*Pollen parent.*—An unnamed Pink Sweetheart seedling of "Garnette."
Propagation: Holds its distinguishing characteristics through succeeding propagations by grafting.

*Flower*

Locality where grown and observed: Richmond, Indiana.
Flowers borne: From 1 to 3 to a stem (usually disbudded commercially to a single flower); on moderately strong stems of from short to medium length.

Quantity of Bloom: Abundant, in greenhouse.
Continuity: Continuous, in greenhouse.
Fragrance: Moderate, in greenhouse. Nature—tea.
Bud:
*Peduncle.*—From short to medium length; small diameter; erect; medium strong. Bark—entirely smooth, except for prickles; color—Moderate Yellow Green, Plate 5GY 5/6 N. Thorns—none. Prickles—several; color—Pale Veronese Green, Plate XVIII R, shaded to a brownish tinted base. Hairs—none.
*Before calyx breaks.*—Size—small. Form—long pointed to ovoid; with a conspicuous neck; with foliaceous appendages on the surface of the bud; with slender foliaceous parts extending beyond the tip of the bud equal to ¼ to ½ or more of its length. Color—Moderate Yellow Green, Plate 5GY 5/6 N.
*As calyx breaks.*—Color—Carmine Rose, Plate 621 W.
*As first petal opens.*—Size—small. Form—long pointed. Color: outside—Tyrian Rose, Plate 24/3 W, with base Sulphur Yellow, Plate 1/3 W; inside—Neyron Rose, Plate 623/2 W, with base Sulphur Yellow, Plate 1/3 W.
*Opening.*—Opens up well in greenhouse; slightly smaller bud in extreme heat.
Bloom:
*Size (when fully open).*—Medium small; from 3 to 3¾ inches.
*Petalage.*—Very double; from 50 to 60 petals; arranged regularly.
*Form.*—High centered at first and remaining high centered; petals being at first tightly rolled outward, becoming loosely rolled out later at maturity but not down lower than a level plane.
Petals:
*Texture.*—Moderately thin. Inside—satiny. Outside—satiny.
*Shape.*—Outer—from oval to slightly obovate, with apex mucronate, and with from one to several notches. Intermediate—oval apex and slightly mucronate to entire. Inner—oval, with apex mucronate, and with 1, but sometimes 2 or 3 notches of very small size.

This description of a newly opened flower was made from a rose grown in a greenhouse during the month of September at Richmond, Indiana:

*Color.*—Outer petal: outside surface—a little lighter than Rose Pink, Plate 427/2 W, with base Primrose Yellow, Plate 601/3 W; inside surface—Rose Pink, Plate 427/2 W, with base Naples Yellow, Plate 403/3 W. Intermediate petal: outside surface—Neyron Rose, Plate 623/2 W, with base Primrose Yellow, Plate 601/3 W; inside surface—Rose Pink, Plate 427/1 W, with base almost pure white. Inner petal: outside surface—Thulite Pink, Plate XXVII R, with base Naphthalene Yellow, Plate XVI R; inside surface—Rosalane Pink, Plate XXXVI R, with base Naples Yellow, Plate 403/3 W.

This description was made from a rose that was open for three days in a greenhouse during the month of September at Richmond, Indiana:

*Color.*—Outer petal: outside surface—Rose Pink,

Plate 427/3 W, with base almost white; inside surface—Dawn Pink, Plate 523/3 W, with base almost white. Intermediate petal: outside surface—lighter than Neyron Rose, Plate 623/2 W, with base almost white; inside surface—Rose Pink, Plate 427/2 W, with base almost white. Inner petal: outside surface—Neyron Rose, Plate 623/2 W, with base almost white; inside surface—Dawn Pink, Plate 523/3 W, with base almost white.

*General color effect.*—Newly opened flower—slightly lighter than Neyron Rose, Plate 623/2 W. 3-days open—Pale Pink, Plate 2.5R 9/3 N.

*Behavior.*—Persist in greenhouse; fading lighter than Rose Pink, Plate 427/3 W.

*Flower longevity.*—Cut flowers grown in greenhouse and kept at living room temperatures—7 days in April.

*Plant*

Foliage:

*Leaves.*—Compound of 3 to 5 leaflets; normal abundance; moderately small size; moderately wrinkled; medium texture.

*Leaflets.*—Shape—elliptical, with apex from acute to slightly cuspidate. Base—obtuse. Margin—serrate.

*Color.*—Mature: upper surface—a shade lighter than Varley's Green, Plate XVIII R; under surface—lighter than Cedar Green, Plate 80 W. Young: upper surface—Dark Livid Brown, Plate XXXIX R, shaded to Green at midrib; under surface—Deep Livid Brown, Plate XXXIX R, shaded with green at midrib.

*Rachis (the supporting stem of the compound leaf).*—From light to medium. Upper side—grooved; almost smooth. Under side—very sparsely prickly.

*Stipulses.*—Short; very narrow; with short points turning out at an angle of from less than 45° up to 90°.

Growth (in greenhouse):

*Habit.*—Upright; much-branched.

*Growth.*—Free; vigorous.

*Canes.*—Small diameter.

*Main stems.*—Color—slightly lighter than Forest Green, Plate XVII R. Thorns—from few to several; medium length; straight; with narrow base; color—Burnt Umber, Plate XXVIII R. Prickles—none. Hairs—none.

*Branches.*—Color—Spinach Green, Plate 0960/1 W. Thorns—few; medium length; straight; with short narrow base; color—base slightly lighter than Pale Cinnamon, Plate XXIX R, shaded to a Deep Sea-Foam Green, Plate XXXI R at tip. Prickles—none. Hairs—none.

*New shoots.*—Color—Cerro Green, Plate V R, with a suffusion of Haematite Red, Plate XXVII R. Thorns—from few to several; color—slightly darker than Deep Corinthian Red, Plate XXVII R, with thorn tips shaded from Chalcedony Yellow, Plate XVII R to Courge Green, Plate XVII R. Prickles—none. Hairs—none.

*Reproductive Organs*

Stamens: Medium number; arranged regularly about pistils.

Filaments: Short; most with anthers. Color—Citron Yellow, Plate XVI R.

Anthers: From medium to small; all open at once. Color—Light Cadmium, Plate IV R.

Pollen: Moderate quantity. Color—slightly darker than Light Cadmium, Plate IV R.

Pistils: Medium number.

Styles: Fairly even; medium length but longer than filaments; moderately thin; bunched; columnar. Color—Picric Yellow, Plate IV R.

Stigma: Color—Blood Red, Plate 820/2 W.

Ovaries: Some protruding from calyx.

Hips: Medium length; ovoid; with inconspicuous neck; pear-shaped; smooth; walls thin and slightly fleshy.

Sepals: Permanent; moderately short.

Seeds: Moderate number; from small to medium size.

I claim:

A new and distinct variety of rose plant of the floribunda class, substantially as herein shown and described, characterized particularly as to novelty by the unique combination of good length of its flower stems and their consequent suitability for cut flowers, attractive and well formed buds of large and commercially usable size, a distinctive and attractive pink general color tonality of the flowers, and good keeping qualities of the flowers.

No references cited.